United States Patent
Gao et al.

(10) Patent No.: US 12,426,578 B1
(45) Date of Patent: Sep. 30, 2025

(54) GENOMIC MATING METHOD FOR HUAXI CATTLE BASED ON WHOLE GENOME SINGLE NUCLEOTIDE POLYMORPHISM INFORMATION AND APPLICATION THEREOF

(71) Applicant: Beijing Institute of Animal Husbandry and Veterinary Medicine, Chinese Academy of Agricultural Sciences, Beijing (CN)

(72) Inventors: Xue Gao, Beijing (CN); Junya Li, Beijing (CN); Yuanqing Wang, Beijing (CN); Bo Zhu, Beijing (CN); Zezhao Wang, Beijing (CN); Yan Chen, Beijing (CN); Lupei Zhang, Beijing (CN); Lingyang Xu, Beijing (CN)

(73) Assignee: Beijing Institute of Animal Husbandry and Veterinary Medicine, Chinese Academy of Agricultural Sciences, Beijing (CN)

( * ) Notice: Subject to any disclaimer, the term of this patent is extended or adjusted under 35 U.S.C. 154(b) by 0 days.

(21) Appl. No.: 18/948,372

(22) Filed: Nov. 14, 2024

(30) Foreign Application Priority Data

Jul. 9, 2024 (CN) .......................... 202410915694.5

(51) Int. Cl.
G01N 33/48 (2006.01)
A01K 67/02 (2006.01)
G01N 33/50 (2006.01)
G16B 20/20 (2019.01)

(52) U.S. Cl.
CPC .............. *A01K 67/02* (2013.01); *G16B 20/20* (2019.02)

(58) Field of Classification Search
CPC ................................ A01K 67/02; G16B 20/20
See application file for complete search history.

(56) References Cited

FOREIGN PATENT DOCUMENTS

| CN | 111243667 A | 6/2020 |
|---|---|---|
| CN | 113517020 A | 10/2021 |
| CN | 116863998 A | 10/2023 |

OTHER PUBLICATIONS

Berry et al. Genetics and genomics of reproductive performance in dairy and beef cattle. Animal, vol. 8, supplement 1, pp. 105-121. (Year: 2014).*

(Continued)

*Primary Examiner* — Russell S Negin

(57) ABSTRACT

Disclosed are a genomic mating method for Huaxi cattle based on whole genome single nucleotide polymorphism (SNP) information and an application thereof. The method includes the following specific steps: step 1, extracting deoxyribonucleic acid (DNA) from to-be-hybridized Huaxi cattle individuals for genotyping; step 2, performing genotype data imputation to obtain high-density chip data; step 3, calculating an additive genetic relationship matrix, utilizing genomic best linear unbiased prediction (GBLUP) to obtain genomic estimated breeding values of five important economic traits of a to-be-hybridized Huaxi cattle population, and calculating a comprehensive selection index of the individuals; and step 4, using a genetic algorithm to construct a population optimal mating combination list. In the present invention, the breeding cost is greatly saved and an inbreeding level of offspring populations is reduced.

2 Claims, 2 Drawing Sheets

(56) References Cited

OTHER PUBLICATIONS

Wang et al. Evaluation of genomic mating approach based on genetic algorithms for long-term selection in Huaxi cattle. BMC Genomics, Nov. 26, 2024, vol. 25, article 1140, 12 pages. (Year: 2024).*

* cited by examiner

GENOMIC MATING METHOD FOR HUAXI CATTLE BASED ON WHOLE GENOME SINGLE NUCLEOTIDE POLYMORPHISM INFORMATION AND APPLICATION THEREOF

CROSS-REFERENCE TO RELATED APPLICATION

This application claims priority of Chinese Patent Application No. 202410915694.5, filed on Jul. 9, 2024, the entire contents of which are incorporated herein by reference.

TECHNICAL FIELD

The present disclosure belongs to the technical field of animal breeding, and particularly relates to a genomic mating method for Huaxi cattle based on whole genome single nucleotide polymorphism (SNP) information and an application thereof.

BACKGROUND

Huaxi cattle, a new specialized beef cattle, has been bred by Institute of Animal Sciences, Chinese Academy of Agricultural Sciences over more than 40 years. In 2021, the Huaxi cattle was approved by the National Livestock and Poultry Genetic Resources Committee and obtained new breed certificate of the national livestock and poultry. The Huaxi cattle has the characteristics of fast growth, high feed conversion rate, high net meat rate, good meat production and reproduction performance, and strong stress resistance. Compared with the same type of beef cattle breeds in the world, the daily gain, dressing percentage and pure meat percentage of Huaxi cattle are at the international advanced level. However, the performance of the breed still needs continuous breeding improvement to achieve sustainable genetic gain. In Huaxi cattle breeding, an excellent breeding bull will be bred with hundreds of cows through artificial insemination. Although this method can rapidly improve the population genetic gain, it will cause the homozygous accumulation of harmful genes and the loss of rare genes after multi-generation breeding, resulting in inbreeding depression, which is not conducive to the breeding process. Therefore, many considerations are needed in breeding Huaxi cattle.

With the development and use of high-throughput sequencing technology and chip technology, genomic mating, as a more reliable and accurate breeding method, is a technological innovation to carry out accurate breeding and mating and accelerate the cultivation of high-quality beef cattle populations. In the late 20th century, researchers at home and abroad proposed a method of utilizing a genealogical relationship to implement optimal mating, such as sequential programming, and optimal contribution selection (OCS). With the wide application of genome molecular markers (such as SNP), the utilization of genome information to optimize mating has become the focus of breeding research. At present, researchers at home and abroad use a variety of methods to integrate genome information to optimize the mating, such as linear programming (LP), genomic optimal contribution selection (GOCS), minimum co-ancestry mating (MC), and minimizing the covariance between ancestral contributions (MCAC), which can accelerate the genetic gain and effectively control the inbreeding level of populations. Compared with genomic selection, genomic mating utilizes genome information to track the inheritance of chromosome segments, to improve the accuracy of Mendelian sampling estimation of parents and its relationship with the genetic contribution of parents, transferring the focus of problems to mating, which is more helpful to achieve the goal of efficient breeding. To date, there has been no report on the genomic mating of Huaxi cattle.

SUMMARY

The technical problem to be solved by the present disclosure is to address the above-mentioned deficiencies of the prior art, and a genomic mating method for Huaxi cattle based on whole genome SNP information and an application thereof are provided to accelerate the breeding process of Huaxi cattle.

In order to achieve the above object, the present disclosure provides the following technical solutions. A genomic mating method for Huaxi cattle based on whole genome SNP information specifically includes the following steps:

step 1, extracting deoxyribonucleic acid (DNA) from to-be-hybridized Huaxi cattle individuals, utilizing a Cattle110K gene chip for genotyping, and performing data processing and quality control;

step 2, performing genotype data imputation to obtain 770K high-density chip data, performing numerical processing on the genotype data after imputation, and utilizing PLINK software to convert genotypes AA, Aa and aa into 0, 1 and 2, respectively;

step 3, calculating an additive genetic relationship matrix (G matrix) according to a VanRaden algorithm, utilizing genomic best linear unbiased prediction (GBLUP) to obtain genomic estimated breeding values of five important economic traits of a to-be-hybridized Huaxi cattle population, and calculating a comprehensive selection index of the individuals according to the genomic estimated breeding value of each of the traits; and step 4, constructing all possible mating combinations, calculating, according to genotype data of bulls and cows of each mating pair and the additive genetic relationship matrix, an expected comprehensive selection index value and an inbreeding coefficient of an offspring population of each mating pair under the condition of considering mutations by using the genetic algorithm, optimizing a mating combination between to-be-hybridized cows and candidate bulls according to the two indexes, and finally providing a mating list of the to-be-hybridized cows with the optimal candidate bulls.

In a further solution of the present disclosure: the quality control in step 1 is that only autosomal sites are retained, sites with a success rate of genotyping less than 90%, a minimum allele frequency (MAF) of less than 0.05 and a Hardy-Weinberg (HW) equilibrium test of less than 0.000001 are eliminated, and the gene chip is a Cattle110K chip.

In a further solution of the present disclosure: the five important economic traits in step 3 include carcass weight, calving ease, weaning weight, average daily gain and a dressing percentage, the additive genetic relationship matrix (G matrix) is calculated according to the VanRaden algorithm, and the genomic estimated breeding value is calculated using a GBLUP model, the model being as follows:

$$y = Xb + Za + e$$

where y represents a phenotypic observation value vector; X is an n×f dimensional incidence matrix; b is an f dimensional fixed effect vector; f is the number of fixed effects; Z is a structural matrix associated with a; a represents an additive effect vector and obeys the normal distribution of N (0, G$\sigma_g^2$), G being an additive genome relationship matrix, and $\sigma_g^2$ being an additive genetic variance; and e is a residual vector and obeys the normal distribution of N (0, I$\sigma_e^2$).

In a further solution of the present disclosure: in step 4, the calculating an expected comprehensive selection index value and an inbreeding coefficient of an offspring population of each mating pair under the condition of considering mutations by using an optimized genetic algorithm model, optimizing a mating combination between to-be-hybridized cows and candidate bulls according to the two indexes, and finally providing a mating list of the to-be-hybridized cows with the optimal candidate bulls includes the following optimized genetic algorithm model:

$$\underset{P}{\text{minimize}} r(\lambda_1, \lambda_2, p) = -\text{Risk}(\lambda_1, p) + \lambda_2 * \text{Inbreeding}(P)$$

where $\lambda_2 \geq 0$ is a parameter controlling the degree of inbreeding in offspring, and $\lambda_1$ is a parameter controlling the degree of allele heterozygosity; and a specific calculation model of genetic gain and an inbreeding coefficient is as follows:

$$\text{Inbreeding}(P) = 1'_{N_c}(PGP' + D)1'_{N_c}$$

$$\text{Gain}(P) = 1'_{N_c}PMa$$

where P is a mating matrix of $N_c \times N$, N being the number of parents and $N_c$ being the number of offspring; G is an additive genome relationship matrix; D is Mendelian sampling deviation; M is a genotype matrix; and a is a labeling effect.

In a further solution of the present disclosure: in step 4, the optimal mating is performed according to a comprehensive selection index of to-be-hybridized parental individuals, and a formula of the Genomic China Beef Index (GCBI) is as follows:

$$GCBI = 100 + \left( -5 \times \frac{GEBV_{CE}}{1.30} + 35 \times \frac{GEBV_{WWT}}{17.7} + \right.$$
$$\left. 20 \times \frac{GEBV_{DG_F}}{0.11} + 25 \times \frac{GEBV_{CW}}{16.4} + 15 \times \frac{GEBV_{DP}}{0.13} \right)$$

where $GEBV_{CE}$ is a genomic estimated breeding value of a calving ease; $GEBV_{WWT}$ is a genomic estimated breeding value of a weaning weight, and a weaning weight is uniformly corrected to a 6-month-old weight; $GEBV_{DGF}$ is a genomic estimated breeding value of a daily gain in a fattening period; $GEBV_{CW}$ is a genomic estimated breeding value of a carcass weight; and $GEBV_{DP}$ is a genomic estimated breeding value of a dressing percentage.

An object of the present disclosure is an application of the method described in the above technical solution in the genomic mating of Huaxi cattle.

The present disclosure has the following beneficial effects:

In the present disclosure, a genomic mating method for Huaxi cattle based on whole genome SNP information is established, which greatly saves breeding costs and maintains long-term sustainable genetic gain. The present disclosure can also fill the blank of genomic mating of beef cattle in China, solve the problem of how to mating and combine after genomic selection in beef cattle breeding process, provide technical means for beef cattle breeding with high efficiency and quality, accelerate the beef cattle breeding process, promote the rapid development of beef cattle industry, and have great application value and promotion prospects.

BRIEF DESCRIPTION OF THE DRAWINGS

For ease of explanation, the present disclosure is described in detail in the following detailed description and accompanying drawings.

DETAILED DESCRIPTION

The specific embodiments of the present disclosure will be described below, and the technical solutions of the present disclosure will be further described with reference to the accompanying drawings; but the present disclosure is not limited to these embodiments. In the following description, specific details, such as specific configurations, are provided only to help fully understand the embodiments of the present disclosure. Accordingly, it is clear to those skilled in the art that various changes and modifications can be made to the embodiments described herein without departing from the scope and spirit of the present disclosure.

Unless otherwise specified, the technical means used in the embodiments are conventional and well known to those skilled in the art. Chemical reagents used in the embodiments are commercially available.

A genomic mating method for Huaxi cattle populations based on whole genome SNP information by the present disclosure includes the following steps.

Figure 1:
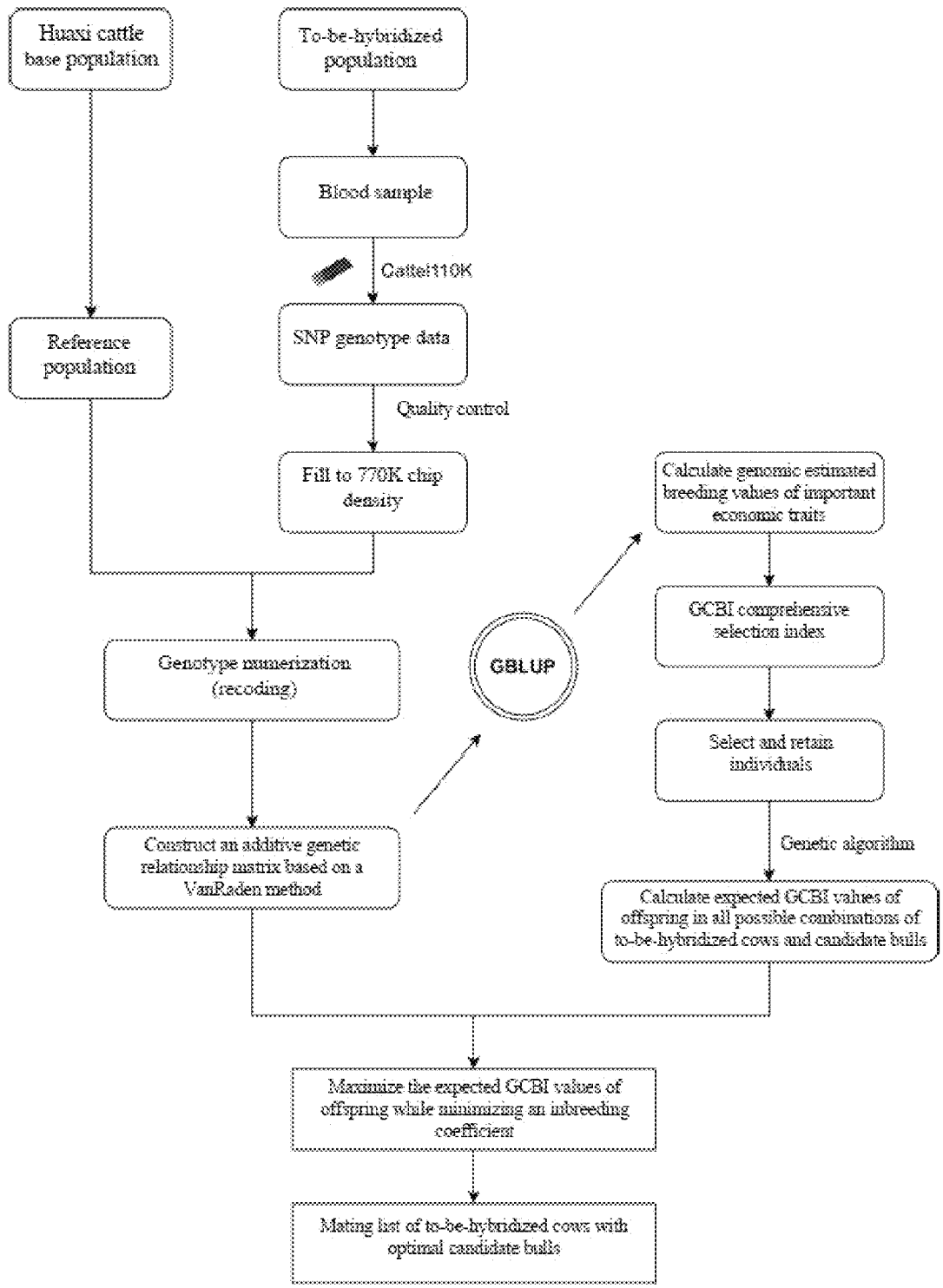
FIG. 1 is a flow chart of a genomic mating method for Huaxi cattle based on whole genome SNP information provided in an embodiment of the present disclosure.

FIG. 1 shows a flow chart of the genomic mating of Huaxi cattle populations based on whole genome SNP data according to the present disclosure.

I. Blood samples are collected from each cow of to-be-hybridized Huaxi cattle populations and frozen for preservation, and DNA is extracted, which is subjected to genotyping by using a Cattle110K gene chip. PLINK 1.0 software is adopted to perform processing and quality control of the data after genotyping, and the quality control standard is as follows: (1) located on an autosome; (2) the MAF is greater than 0.05; (3) a call rate of each SNP marker is greater than 0.9; and (4) a HW equilibrium test P>1×10$^{-6}$.

II. According to the 770K chip data of 3928 cattle in a previously established Huaxi cattle reference population, the 110K chip data of the to-be-hybridized population is imputed to 770K high-density chip data (774,660SNPs) using Beagle software. The imputed genotype data is numerically processed using PLINK 1.0 to re-encode genotypes AA, Aa and aa as 0, 1, and 2, respectively.

III. The data obtained in step 2 is utilized, and an additive genetic relationship matrix is constructed using a VanRaden model and an A. mat function in an rrBLUP software package. According to genotype and phenotype data of a Huaxi cattle reference population, an Asreml-R software package is employed to perform GBLUP for genomic estimated breeding values of five important economic traits (carcass weight, calving ease, weaning weight, average daily gain and dressing percentage) of the to-be-hybridized population, and a comprehensive selection index is calculated.

$$GCBI = 100 + \left(-5 \times \frac{GEBV_{CE}}{1.30} + 35 \times \frac{GEBV_{WWT}}{17.7} + 20 \times \frac{GEBV_{DG_F}}{0.11} + 25 \times \frac{GEBV_{CW}}{16.4} + 15 \times \frac{GEBV_{DP}}{0.13}\right)$$

IV. The first 10% of bulls and the first 90% of cows with GCBI value are selected and retained, the corresponding genotype data are extracted by using PLINK 1.0, and the expected GCBI value and inbreeding coefficient of offspring are calculated for all possible pairs based on the optimized genetic algorithm model by using a TrainSel software package. The optimal mating is solved to maximize the expected GCBI value of offspring while minimizing the inbreeding coefficient.

V. A mating list is provided for each to-be-hybridized cow with the optimal candidate bull.

Embodiment 1 Genomic Mating of Huaxi Cattle Based on Whole Genome SNP Information Experimental materials: a total of 137 Huaxi breeding bulls from Tongliao Jingyuan Cattle Breeding Co. Ltd., Henan Dingyuan Cattle Breeding Co. Ltd., and other bull stations, as well as a total of 213 Huaxi cows from Jilin Allgenes Agriculture and Animal Husbandry Technology Development Co. Ltd., were selected.

The specific steps are as follows:

I. Blood samples were collected from all Huaxi cattle via vein, and stored in 5 ml EDTA vacuum anticoagulant blood collection tubes (special blood collection tube from MolBreeding) for frozen preservation. The samples were mailed to Shijiazhuang MolBreeding Biotechnology Co. Ltd., and were registered through a MolBreeding sample delivery management system. Genotype information was obtained for the 110K genome SNP (112,180SNPs).

II. Before the analysis, it was necessary to make quality control on genotype data, and PLINK 1.0 was employed to eliminate the unqualified SNP. The quality control criteria and codes for this study were: plink--cow--file filename--geno 0.1--maf 0.05--hwe 0.000001--recode--out filename. After quality control, 350 Huaxi cattle and 106,658 SNPs remained. After quality control, utilizing a reference panel established by Illumina BovineHD 770K high-density chip data from 5099 Huaxi cattle to perform imputation on the 110K chip data of Huaxi cattle populations, the Beagle software was utilized to perform imputation on the missing SNPs after quality control, following the running commands: java-Xmx1000m-jar unphased-file.bgl out-output niterations=100. The Beagle software was utilized to impute the 110K chip data to 770K high-density chip data (774,660SNPs), following the running commands: java-Xmx1000m-jar gt-filename.vcf ref-imputation_ref.vcf.gz out=filename. The obtained genotype files were re-encoded into data of three typing formats: 0, 1 and 2 using PLINK 1.0 software, following the running commands: plink--cow--vcf filename--recode A--out filename. The transformed genotype data was used for subsequent genomic mating of Huaxi cattle.

III. The VanRaden model was used to construct an additive genetic relationship matrix (G matrix) by utilizing an A.mat function in an rrBLUP software package. The Asreml-R software package was used for genetic evaluation, and the GBLUP model was adopted to calculate the genomic estimated breeding values for five traits (carcass weight, calving ease, weaning weight, average daily gain and dressing percentage) of to-be-hybridized Huaxi cattle. A reference population was selected from a reference population of a total of 3928 Huaxi cattle previously established by Institute of Animal Sciences, Chinese Academy of Agricultural Sciences. According to the calculated genomic estimated breeding values of five traits of each of the individuals of the to-be-hybridized population, the comprehensive selection index GCBI was calculated, and ranked by bulls and cows. The genetic parameters of various traits were shown in Table 1.

TABLE 1

Genetic parameters of various traits

| Traits | Genetic variance | Environmental variance | Phenotypic variance | Heritability ($h^2$) | Accuracy of genomic estimated breeding value |
|---|---|---|---|---|---|
| Calving ease | 1.69 | 5.99 | 7.68 | 0.22 | 0.51 |
| Weaning weight | 594.84 | 780 | 1374.84 | 0.43 | 0.56 |
| Daily gain in Fattening period | 0.0121 | 0.0131 | 0.252 | 0.48 | 0.61 |
| Carcass weight | 268.69 | 328.4 | 597.09 | 0.45 | 0.64 |
| Dressing percentage | 0.0169 | 0.0394 | 0.0563 | 0.3 | 0.52 |

IV. The Huaxi bulls and cows were selected and retained according to the size of GCBI. The selection criteria were: the bull GCBI was greater than 150 and the cow GCBI was greater than 80. Individual IDs and GCBI values selected and retained are shown in Table 2.

TABLE 2

Number and GCBI values of selected and retained bulls and cows

| Bull | | Cow | |
|---|---|---|---|
| ID Number | GCBI value | ID Number | GCBI value |
| 15217181 | 302.06 | 1429 | 200.77 |
| 15419623 | 254.81 | 1779 | 197.75 |
| 15421638 | 245.75 | 1492 | 169.50 |
| 15420645 | 214.85 | 2078 | 165.65 |
| 15420613 | 210.20 | 1230 | 164.22 |
| 15420616 | 197.65 | 1497 | 158.12 |
| 15420635 | 196.29 | 20120701 | 157.94 |
| 15419619 | 192.61 | 1236 | 155.92 |
| 15219124 | 190.54 | 1071 | 153.15 |
| 15420637 | 169.48 | 1753 | 152.54 |
| 15219174 | 155.06 | A051 | 150.73 |
| 15420611 | 154.98 | 2843 | 150.28 |
| 15217191 | 152.68 | . . . | . . . |

V. A total of 13 breeding bulls and 200 cows were obtained for genomic mating. Genotype data of selected and retained bulls and cows was extracted using PLINK 1.0, following the running commands: plink --cow --file filename --keep dam.txt --recode A --out hx_dam, plink --cow --filename --keep sire.txt --recode A --out hx_sire, in which dam.txt and sire.txt were ID lists of the cows and bulls selected and retained, respectively.

VI. The genotypes and corresponding GCBI values of bulls and cows selected and retained in step (4) were input into a TrainSel software package, and the optimized genetic algorithm was utilized for mating. The parameter settings of the genetic algorithm were: npop=200, nelite=10, mutprob=0.01, niterations=800, niterSANN=200, stepSANN-0.01, minitbefstop=200, tolconv=1e-7, nislands=1, mc.cores=1.

VII. The GCBI value scheme maximizing the expectation of offspring was selected from the output results of genetic algorithm, and the mating list of the to-be-hybridized cows with the optimized candidate bulls was obtained (seen in Table 3).

TABLE 3

Mating list of to-be-hybridized cows with the optimized candidate bulls

| Candidate cow number | Candidate cow GCBI value | Candidate bull number | Candidate bull GCBI value |
|---|---|---|---|
| 1429 | 200.77 | 15217191 | 152.68 |
| 1779 | 197.75 | 15419623 | 254.81 |
| 1492 | 169.50 | 15219124 | 190.54 |
| 2078 | 165.65 | 15217181 | 302.06 |
| 1230 | 164.22 | 15219174 | 155.06 |
| 1497 | 158.12 | 15419619 | 192.61 |
| 20120701 | 157.94 | 15420645 | 214.85 |
| 1236 | 155.92 | 15420611 | 154.98 |
| 1071 | 153.15 | 15219124 | 190.54 |
| 1753 | 152.54 | 15420611 | 154.98 |
| A051 | 150.73 | 15420613 | 210.20 |
| 2843 | 150.28 | 15217181 | 302.06 |
| A120 | 150.11 | 15217181 | 302.06 |
| A047 | 148.69 | 15420611 | 154.98 |
| 21010902 | 147.66 | 15219124 | 190.54 |
| 1469 | 147.47 | 15420616 | 197.65 |
| 1965 | 145.91 | 15420635 | 196.29 |
| 1374 | 145.65 | 15421638 | 245.75 |

Figure 2:
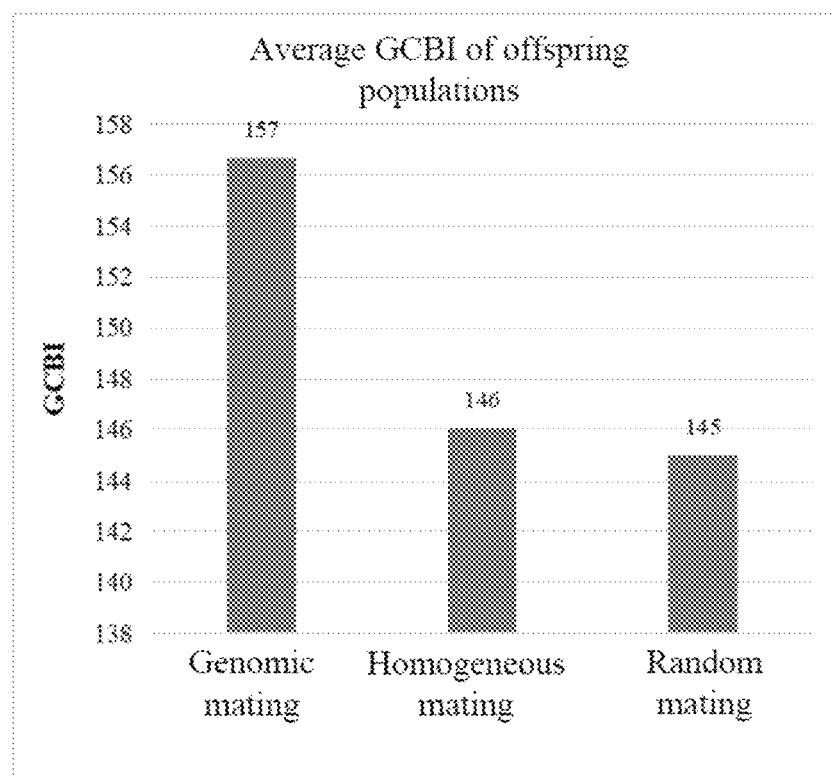
FIG. 2 is a schematic diagram comparing GCBI for offspring populations in different mating schemes.

VIII. Genomic mating effect: to further illustrate the superiority of the genomic mating method, in this data set, the GCBI and inbreeding level of the offspring of genomic mating, homogeneous mating and random mating were evaluated. The results show that the genomic mating scheme has obtained the maximum expected GCBI value of offspring, with the greatest genetic gain (FIG. 2), while has a lower average inbreeding level of the offspring populations than that of the traditional mating scheme (Table 4). The implementation of genomic mating can rapidly improve the genetic gain of Huaxi cattle populations, highlighting the importance of genome information.

TABLE 4

Comparison of average GCBI and inbreeding levels of offspring populations from different mating schemes

| Mating scheme | Average GCBI (±standard deviation) | Average inbreeding coefficient (±standard deviation) |
|---|---|---|
| Genomic mating | 156.663 ± 0.100 | 0.030 ± 0.000 |
| Homogeneous mating | 146.038 ± 0.100 | 0.032 ± 0.000 |
| Random mating | 145.786 ± 0.090 | 0.031 ± 0.000 |

The present disclosure can fill the blank of genomic mating of beef cattle in China, solve the problem of how to mating and combine after genomic selection in beef cattle breeding process, provide technical means for beef cattle breeding with high efficiency and quality, accelerate the beef cattle breeding process, promote the rapid development of beef cattle industry, and have great application value and promotion prospects.

Those skilled in the technical field to which the present application belongs can make various modifications or supplements to the described specific embodiments or substitute them in a similar way, without departing from the inventive concept of the present application or exceeding the scope defined by the appended claims.

The invention claimed is:

1. A mating method for Huaxi cattle based on whole genome single nucleotide polymorphism (SNP) information, comprising the following specific steps:

step 1, extracting deoxyribonucleic acid (DNA) from to-be-hybridized Huaxi cattle individuals, utilizing a Cattle110K gene chip for genotyping, and performing data processing and quality control;

step 2, performing genotype data imputation to obtain 770K high-density chip data, performing numerical processing on the genotype data after imputation, and utilizing a whole genome data analysis toolset to convert genotypes AA, Aa and aa into 0, 1 and 2, respectively;

step 3, calculating an additive genetic relationship matrix according to a VanRaden algorithm, utilizing genomic best linear unbiased prediction (GBLUP) to obtain genomic estimated breeding values of five important economic traits of a to-be-hybridized Huaxi cattle population, and calculating a comprehensive selection index of the individuals according to the genomic estimated breeding value of each of the traits; and step 4, constructing a population optimal mating combination list by using a genetic algorithm, calculating, according to genotype data of bulls and cows of each mating pair and the additive genetic relationship matrix, an expected comprehensive selection index value and an inbreeding coefficient of an offspring population of each mating pair under the condition of considering mutations by using the genetic algorithm, optimizing a mating combination between to-be-hybridized cows and candidate bulls according to the expected comprehensive selection index value and the inbreeding coefficient, and finally providing a mating list of the to-be-hybridized cows with optimal candidate bulls;

wherein the five important economic traits in step 3 comprise carcass weight, calving ease, weaning weight, average daily gain and a dressing percentage, the additive genetic relationship matrix is calculated according to the VanRaden algorithm, and the genomic estimated breeding value is calculated using a GBLUP model, the model being as follows:

$$y=Xb+Za+e$$

where y represents a phenotypic observation value vector; X is an n×f dimensional incidence matrix; b is an f dimensional fixed effect vector; f is the number of fixed effects; Z is a structural matrix associated with a; a represents an additive effect vector and obeys the normal distribution of N (0, G$\sigma_g^2$), G being an additive genome relationship matrix, and $\sigma_g^2$ being an additive genetic variance; and e is a residual vector and obeys the normal distribution of N (0, I$\sigma_e^2$);

wherein in step 4, the calculating an expected comprehensive selection index value and an inbreeding coefficient of an offspring population of each mating pair under the condition of considering mutations by using an optimized genetic algorithm model, optimizing a mating combination between to-be-hybridized cows and candidate bulls according to the expected comprehensive selection index value and the inbreeding coefficient, and finally providing a mating list of the to-be-hybridized cows with the optimal candidate bulls comprises the following optimized genetic algorithm model:

$$\underset{P}{\text{minimize}}\, r(\lambda_1, \lambda_2, p) = -\text{Risk}(\lambda_1, p) + \lambda_2 * \text{Inbreeding}(P)$$

where $\lambda_2 \geq 0$ is a parameter controlling the degree of inbreeding in offspring, and $\lambda_1$ is a parameter controlling the degree of allele heterozygosity; and a specific calculation model of genetic gain and an inbreeding coefficient is as follows:

Inbreeding$(P) = 1'_{N_c}(PGP' + D)1'_{N_c}$

Gain$(P) = 1'_{N_c} PMa$ where P is a mating matrix of $N_c \times N$, N being the number of parents and $N_c$ being the number of offspring; G is an additive genome relationship matrix; D is Mendelian sampling deviation; M is a genotype matrix; and a is a labeling effect;

wherein the optimal mating is performed according to a comprehensive selection index of to-be-hybridized parental individuals, and a formula of the comprehensive selection index is as follows:

$$GCBI = 100 + \left(-5 \times \frac{GEBV_{CE}}{1.30} + 35 \times \frac{GEBV_{WWT}}{17.7} + 20 \times \frac{GEBV_{DG_F}}{0.11} + 25 \times \frac{GEBV_{CW}}{16.4} + 15 \times \frac{GEBV_{DP}}{0.13}\right)$$

where $GEBV_{CE}$ is a genomic estimated breeding value of a calving ease; $GEBV_{WWT}$ is a genomic estimated breeding value of a weaning weight, and a weaning weight is uniformly corrected to a 6-month-old weight; $GEBV_{DGF}$ is a genomic estimated breeding value of a daily gain in a fattening period; $GEBV_{CW}$ is a genomic estimated breeding value of a carcass weight; and $GEBV_{DP}$ is a genomic estimated breeding value of a dressing percentage.

2. The mating method for Huaxi cattle based on whole genome SNP information according to claim 1, wherein the quality control in step 1 is that only autosomal sites are retained, sites with a success rate of genotyping less than 90%, a minimum allele frequency (MAF) of less than 0.05 and a Hardy-Weinberg (HW) equilibrium test of less than 0.000001 are eliminated, and the genotyping is performed using the Cattle110K chip.

* * * * *